(12) United States Patent
Humer et al.

(10) Patent No.: US 8,541,553 B2
(45) Date of Patent: Sep. 24, 2013

(54) ANTIBODIES SPECIFIC FOR THE MELANOMA-ASSOCIATED ENDOGENOUS RETROVIRUS (MERV) ENVELOPE GLYCOPROTEIN

(75) Inventors: Johannes Humer, Vienna (AT); Bernd Mayer, Vienna (AT); Thomas Muster, Vienna (AT); Andrea Waltenberger, Horn (AT)

(73) Assignee: Baxter Healthcare SA, Glattpark (Opfikon) (CH)

( * ) Notice: Subject to any disclaimer, the term of this patent is extended or adjusted under 35 U.S.C. 154(b) by 510 days.

(21) Appl. No.: 12/601,780

(22) PCT Filed: May 23, 2008

(86) PCT No.: PCT/EP2008/056359
§ 371 (c)(1),
(2), (4) Date: Nov. 24, 2009

(87) PCT Pub. No.: WO2008/142157
PCT Pub. Date: Nov. 27, 2008

(65) Prior Publication Data
US 2010/0136518 A1    Jun. 3, 2010

Related U.S. Application Data

(60) Provisional application No. 60/939,997, filed on May 24, 2007.

(30) Foreign Application Priority Data

May 24, 2007 (AT) .................................. A 830/2007
Feb. 1, 2008 (AT) .................................. A 160/2008

(51) Int. Cl.
*C07K 16/00* (2006.01)
*C12N 5/07* (2010.01)
*A61K 39/42* (2006.01)
*A61K 39/21* (2006.01)

(52) U.S. Cl.
USPC ................ 530/388.35; 435/339.1; 424/147.1; 424/207.1

(58) Field of Classification Search
None
See application file for complete search history.

(56) References Cited

FOREIGN PATENT DOCUMENTS

| WO | WO 03/022867 | 3/2003 |
|---|---|---|
| WO | WO 03/029460 | 4/2003 |
| WO | WO 2006/072620 | 7/2006 |
| WO | WO 2006/103562 | 10/2006 |
| WO | WO 2006/119527 | 11/2006 |
| WO | WO 2007/137279 | 11/2007 |

OTHER PUBLICATIONS

Chen, C., et al., 1995, Enhancement and destruction of antibody function by somatic mutation: unequal occurrence is controlled by V gene combinatorial associations, The EMBO J. 14(12):2784-2794.*
Xiang, J., et al., 1991, Modification in framework region I results in a decreased affinity of chimeric anti-TAG72 antibody, Mol. Immunol. 28(1/2):141-148.*
J. Humer et al., Cancer Research, vol. 66, No. 3, pp. 1658-1663 (2006).
T Muster et al., Cancer Research, vol. 63, No. 24, pp. 8735-8741 (2003).
Büscher et al., Melanoma Res. 16, 223-34 (2006).
Balch C M, et al., CA Cancer J Clin, 54, 131-49 (2004).
Written Opinion for International Patent Application No. PCT/EP2008/056359, Sep. 16, 2008.
International Search Report for International Patent Application No. PCT/EP2008/056359, Sep. 16, 2008.
International Preliminary Examination Report for International Patent Application No. PCT/EP2008/056359, Nov. 24, 2009.
Communication from the European Patent Office for European Patent Application No. 08 759 960.1-1222, Apr. 9, 2010.

* cited by examiner

*Primary Examiner* — Jeffrey S. Parkin
(74) *Attorney, Agent, or Firm* — Michael Fedrick; Loza & Loza, LLP

(57) ABSTRACT

The present invention provides antibodies, or fragments thereof, for isolating and/or identifying epitopes of an endogenous retrovirus, preferably of a melanoma associated endogenous retrovirus, and hybridoma cells producing said antibodies. The antibodies are useful especially for the treatment and diagnosis of cancer. Further, the present application covers diagnostic kits for the detection of cancer cells, especially of melanoma cells and methods for cancer diagnosis using said antibodies.

2 Claims, 6 Drawing Sheets

ANTIBODIES SPECIFIC FOR THE MELANOMA-ASSOCIATED ENDOGENOUS RETROVIRUS (MERV) ENVELOPE GLYCOPROTEIN

This application is the U.S. national stage of International Patent Application No. PCT/EP2008/056359, filed on May 23, 2007 and entitled ANTIBODIES USEFUL FOR THERAPY AND DIAGNOSIS OF CANCER, which claims the benefit of priority from the following patent applications: U.S. Patent Application No. 60/939,997, filed on May 24, 2007; Austrian Patent Application No. A8302007, filed on May 24, 2007; and Austrian Patent Application No. A1602008, filed on Feb. 1, 2008. The disclosures of the foregoing applications are incorporated herein by reference in their entirety.

The present invention provides an antibody, or fragment thereof, for isolating and/or identifying epitopes of an endogenous retrovirus, preferably of a melanoma associated endogenous retrovirus, which has the same binding specificity as an antibody produced by the hybridoma cell line DSM ACC2842 or an antibody as produced by the hybridoma cell line DSM ACC2879 and hybridoma cells producing said antibodies. Alternatively, the antibodies of the invention can compete with the antibody produced by the hybridoma cell line DSM ACC2842 or the antibody as produced by the hybridoma cell line DSM ACC2879 for binding to epitopes of an endogenous retrovirus.

The antibodies are useful especially for the treatment and diagnosis of cancer. Further, the present application covers diagnostic kits for the detection of cancer cells, especially of melanoma cells and methods for cancer diagnosis using said antibodies.

Cancer is the general name for over 100 medical conditions involving uncontrolled and dangerous cell growth. Cancer of skin, bladder, breast, colon, lung and pancreas are diagnosed with the greatest frequency and are referred as common cancer.

Melanoma is a cancer of the skin, up to 30% of the patients will develop systemic metastasis and the majority will die (Kirkwood et al.). Classic modalities of treating melanoma include surgery, radiation and chemotherapy. Skin cancer is a disease that develops slowly and can be prevented by monitoring lesions with potential to become cancerous through routine screening. There is, nevertheless, a limit to the amount of time, money or inconvenience that a basically healthy patient is willing to dedicate to routine screening procedures. Therefore, screening must be able to reliably identify lesions containing dangerous tumor cells and differentiate them from benign nevi (moles) quickly, inexpensively and safely.

In Muster et al. (Cancer Res., 2003, 63(24): 8735) a new group of melanoma-associated antigens was presented, MERV (melanoma-associated endogenous retrovirus)—an endogenous retrovirus with high homology to HERV-K.

Monoclonal antibodies have a great potential in cancer therapy as they can bind to tumour antigens with great selectivity and can guide cytotoxic activities to the cancerous cells. Also naked antibodies can be used utilising natural defence mechanisms such as antibody dependent cellular cytotoxicity (ADCC) or complement dependent cytotoxicity (CDC) against the tumour cells.

The degree of success in diagnostics and therapies using monoclonal antibodies depends on many factors, but an important factor is the restricted expression of the antigen recognised by the antibody to the tumour cells. Likewise, the extent of crossreactivity of the antibody with other molecular structures and normal tissues is highly important. Thus, the ideal antibody would only bind to antigens expressed on tumour cells and not to any normal cells. Since most, if not all, tumour associated antigens are expressed both on normal as well as tumour cells, the problem in the art has been to develop antibodies towards antigens expressed to a much higher degree on tumour cells than on normal cells.

This is especially needed for diagnosing melanoma cells from biopsy probes.

In view of the difficulties to detect cancer at an early stage and avoiding the receipt of false positive results especially when diagnosing melanoma cells, there is thus a widely recognized need for specific antibodies to identify pathologic skin conditions and particular cancer precursors.

An object of the present invention is to provide antibodies to satisfy the above-mentioned needs.

According to the invention, this object is achieved by means of antibodies, or fragments thereof, which bind to the same antigen as these antibodies or compete with these antibodies in terms of binding to an epitope of MERV.

The inventors have developed antibodies that selectively bind to retroviral epitopes of endogenous retrovirus, preferably of melanoma associated endogenous retrovirus (MERV, Muster et al., see above). It was successfully shown that these antibodies can detect malignant melanoma cells and can be used for cancer therapy, especially for melanoma treatment.

More specifically, the monoclonal antibodies of the invention are produced by a hybridoma cell line deposited as 1A1-5B10-B3 on May 10, 2007 (deposit number DSM ACC2842) or by a hybridoma cell line deposited as anti-MBP-TM clone 33-8-7 on Jan. 16, 2008 (deposit number DSM ACC2879), both deposited at the DSMZ in Germany. All deposits have been performed according to the Budapest Treaty. Further, diagnostic kits comprising said inventive antibody and methods for detecting melanoma cells is also provided by the invention.

FIGURES

Figure 3:
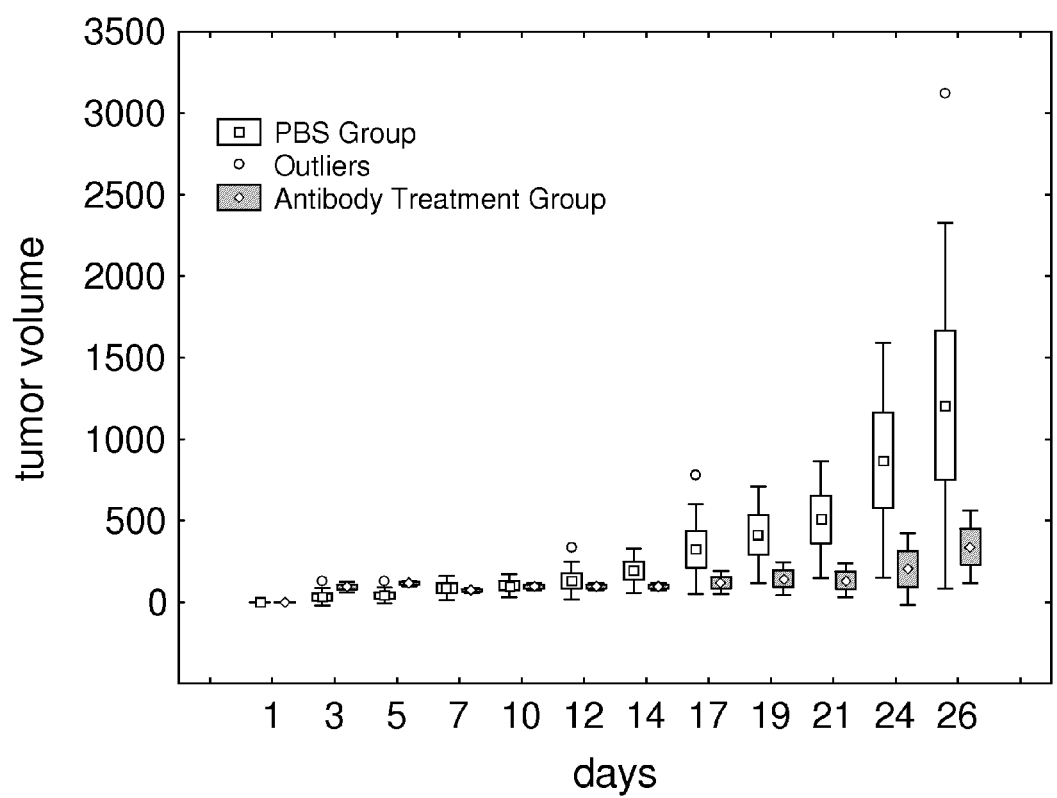

FIG. 3 shows the anti-tumor activity of mAb TM 33-8-7 against melanoma xenografts in vivo. Development of tumor volume ($mm^3$) during treatment (3 days a week, 4 weeks in total) is shown. Treatment starts immediately (day 1) after tumor cell injection (day 0). White bars: PBS control group; shaded bars: mAb TM 33-8-7 group.

Figure 4:
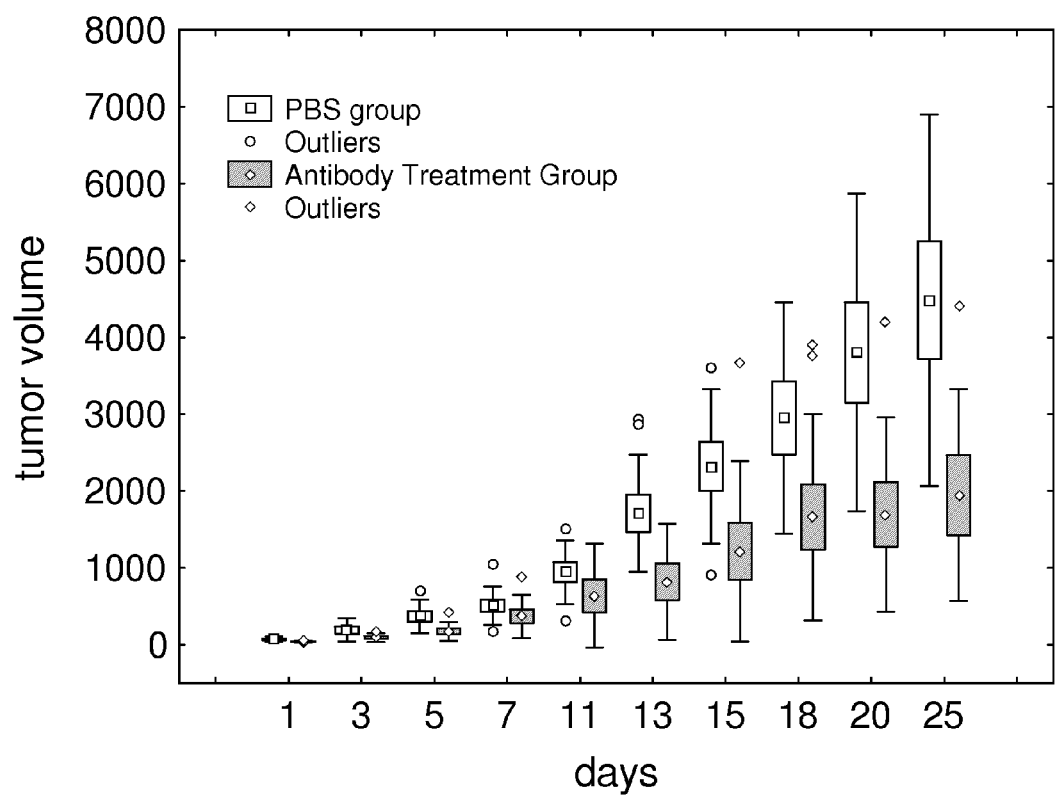

FIG. 4 shows the anti-tumor activity of mAb TM 33-8-7 against melanoma xenografts in vivo. Development of tumor volume ($mm^3$) during treatment (3 days a week, 4 weeks in total) is shown. Treatment starts at a tumor volume of 40 $mm^3$. White bars: PBS control group; shaded bars: mAb TM 33-8-7 group.

Figure 5:
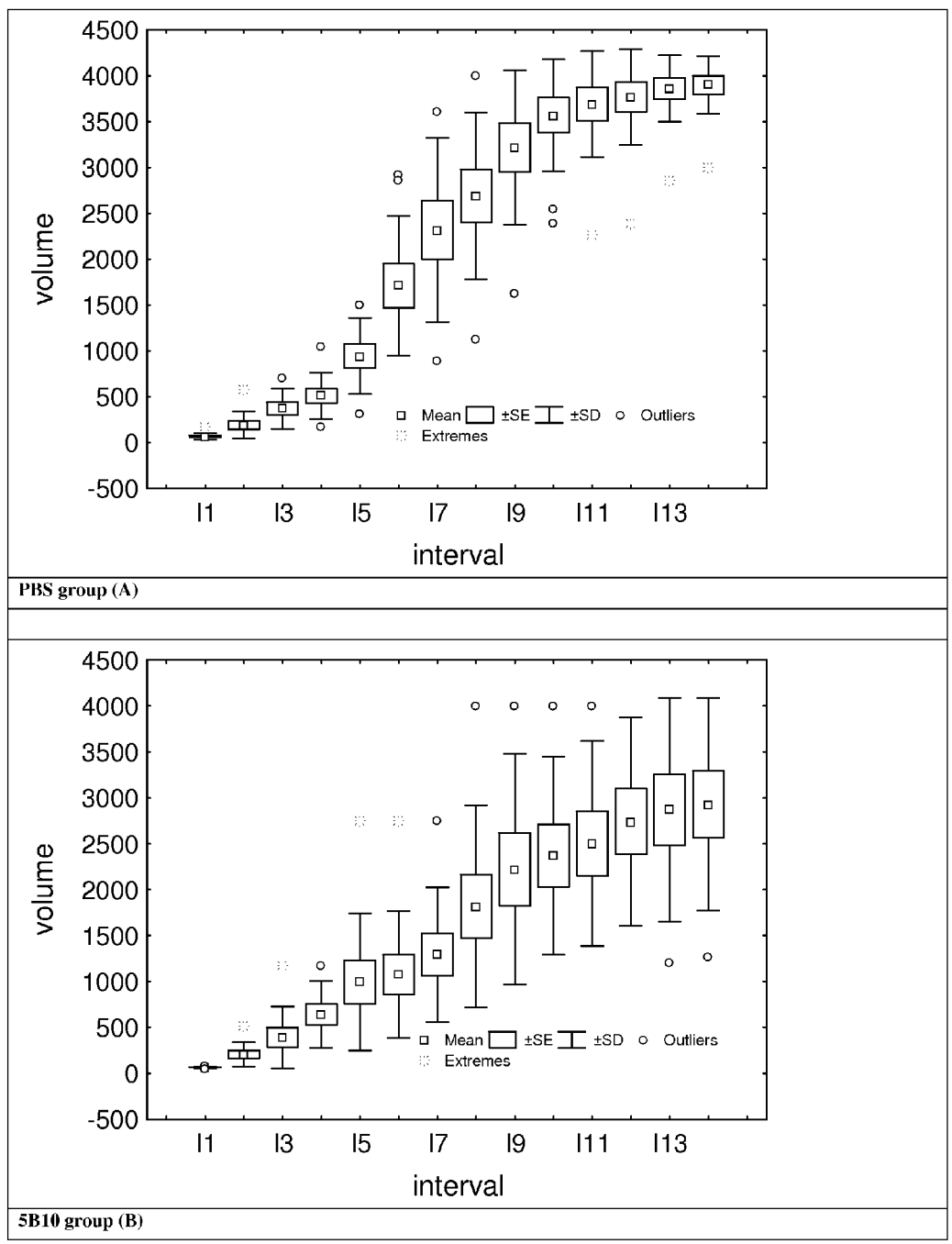

FIG. 5 shows the delay of increase of tumor mass in 5B10 antibody treated mice. in a melanoma xenograft model when therapy was started at a tumor volume of 40 $mm^3$. For analysis tumor volumes >=4000 $mm^3$ were forwarded with this volume also for the subsequent treatment days. In the PBS group a massive expansion of tumor mass is found between day 15 and day 21, whereas in the 5B10 antibody group increase in tumor mass is delayed.

Figure 6:
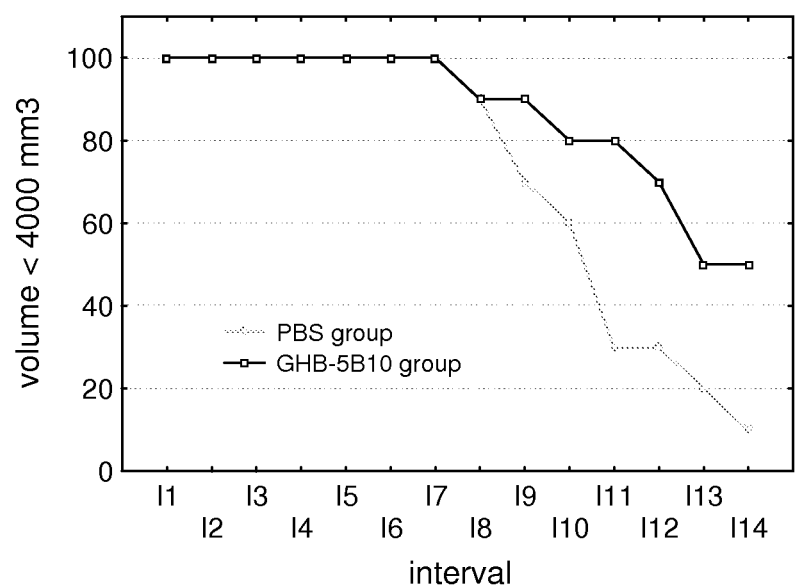

FIG. 6: Number of animals with tumor mass below 4000 mm³ as monitored at each treatment interval. In the PBS group 9 out of 10 animals develop a tumor >4000 mm³, whereas only 5 out of 10 animals develop a tumor >4000 mm³ in the 5B10 antibody group.

The present invention provides antibodies, or fragments thereof, having the same specificity to an epitope of the MERV envelope glycoprotein as an antibody produced by the hybridoma cell line DSM ACC2842 or an antibody as produced by the hybridoma cell line DSM ACC2879 all being deposited at the Deutsche Sammlung von Mikroorganismen and Zellkulturen GmbH (DSMZ).

According to an embodiment of the invention the antibody, or fragment thereof is produced by hybridoma cell lines DSM ACC2842 being deposited on May 10, 2007 (5B10 antibody) or DSM ACC2879 being deposited on Jan. 16, 2008 (TM33-8-7 antibody) or has the same binding specificity.

The antibodies of the invention can be used for identifying and/or isolating epitopes of an endogenous retrovirus, preferably of a melanoma associated endogenous retrovirus.

According to one embodiment of the invention the antibody can bind specifically to an immunodominant region of the surface part of the envelope protein of an endogenous retrovirus, preferably of the envelope of the melanoma associated endogenous retrovirus, preferably to the epitope comprising the amino acid sequence YQRSLKFRPKGKPCPKE (SEQ ID No. 1) or a variant or fragment thereof having at least 80% amino acid identity, preferably at least 90% amino acid identity, preferably at least 95% amino acid identity, preferably a least 99% amino acid identity.

The term "immunodominant regions" according to the invention are defined as peptides or polypeptides corresponding to B-cell epitopes of endogenous retrovirus, preferably of MERV, triggering a humoral immune response. Immunodominant peptides are preferably located in the env protein of MERV. Preferably the immunodominant regions are peptides against which melanoma patients specifically develop antibodies.

Alternatively an antibody is also covered by the invention that binds specifically to the transmembrane region of the envelope protein of an endogenous retrovirus (Accession Number AAY87455 MERV env protein sequence in total), preferably to the epitope comprising the amino acid core sequence HRFQLQCDWNTSDFCITPQIY (SEQ ID No. 2) or a variant or fragment thereof having at least 80% amino acid identity, preferably at least 90% amino acid identity, preferably at least 95% amino acid identity, preferably a least 99% amino acid identity.

Specifically, the transmembrane region of MERV comprises at least part of the amino acid sequence:

```
                                    (SEQ ID. No. 3)
NRSKRFIFTLIAVIMGLIAVTATAAVAGVALHSSVQSVNFVNDWQKNSTR

LWNSQSSIDQKLANQINDLRQTVIWMGDRLMSLEHRFQLQCDWNTSDFCI

TPQIYNESEHHWDMVRRHLQGREDNLTLDISKLKEQIFEASKAHLNLVPG

TEAIAGVADGLANLNPVTWVKTIGSTTIINLILILVCLFCLLLVCRCTQQ

LRRDSDHRERAMMTMAVLSKRKGGNVGKSKRDQIVTVSV
```

Alternatively, the antibodies of the invention can compete with an antibody produced by the hybridoma cell line DSM ACC2842 or an antibody as produced by the hybridoma cell line DSM ACC2879 for binding to epitopes of an endogenous retrovirus, specifically for binding of epitopes of MERV.

"Epitopes" can be substructures of antigens as long as they are immunologically relevant, i.e. are also recognisable by natural or monoclonal antibodies. The term "epitope" as used herein according to the present invention shall mean a molecular structure which may completely be a specific binding structure or be part of a specific binding structure to a binding site of an antibody of the present invention. The epitope will include at least 5 amino acids, preferably 8 to 50 amino acids, and more preferably between about 10-20 amino acids in the peptide. Epitopes can be either continuous or discontinuous epitopes. A continuous epitope is comprised of a single segment of a primary sequence of a polypeptide chain. Linear epitopes can be contiguous or overlapping. Discontinuous epitopes are comprised of amino acids brought together by folding of the polypeptide to form a tertiary structure and the amino acids are not necessarily adjacent to one another in the continuous sequence.

According to the invention also mutants, derivatives or fragments of the antibodies are covered as well. In this connection, "mutants, derivatives or fragments" are understood as meaning any fragment of the antibody which retains the antigen-binding function of the antibody. Preferably, an antibody derivative comprises at least parts of the Fab fragment, preferably together with at least parts of the F(ab)₂ fragment and/or parts of the hinge region and/or the Fc part of a lambda or kappa antibody. As disclosed in WO06072620 the binding region to the epitope can also be located within the structural loops of the Fc part of the antibody. Exemplary antibody molecules are intact immunoglobulin molecules and those portions of an immunoglobulin molecule that contain the paratope, including those portions known as Fab, F(ab)₂ and F (v) and other fragments, such as CDR (complementarity-determining region, hypervariable region) fragments or Fcab™ molecules. The said fragments exhibit the binding specificity of the antibody and can also, for example, be prepared recombinantly using known methods.

Preferably, the antibody is a monoclonal antibody or a fragment thereof.

With the aid of the antibody according to the invention, it is possible to use well-known methods to isolate the corresponding antigen structure and to develop further monoclonal antibodies against the same antigen structure, with the known methods being used in this respect as well.

Because the innate benefit of antibody opsonization is the activation of CDC and ADCC, the inventive antibodies can be modified in a manner that optimizes Fcγ RIII receptor binding but suppresses Fcγ RIIB receptor binding in order to better stimulate the involvement of macrophages and natural killer cells in the antitumor process.

An alternative approach to improving the antitumor activity of monoclonal antibodies involves coupling the targeted antibody to a cytotoxic compound in an attempt to enhance cytotoxicity, in that regard coupling antibodies to radioactive isotopes or covalently attaching conventional chemotherapy drugs onto tumor-selective antibodies are the most frequent strategies.

To gain insight into therapeutic interventions in living mice and humans techniques as bioluminescence imaging (BLI), fluorescence imaging and positron emission tomography (PET) could be applied by use of appropriate mAb.

The specificity of an antibody relates to the antibody's capability of specifically binding to an antigen, more specifically to an epitope as defined above. The specificity of this interaction between the antibody and the antigen (affinity) is characterized by a binding constant or, inversely, by a dissociation constant (Kd).

The binding can be determined quantitatively and/or qualitatively in terms of specificity and/or affinity and/or avidity as used for quality control purposes. Preferably, the binding specificity of antibodies is determined by immunoprecipitation or by an in vitro binding assay, such as radioimmunoassay (RIA) or enzyme-linked immunoabsorbent assay (ELISA). Such techniques and assays are known in the art.

For instance, to determine whether an antibody has the same specificity as the antibodies produced by hybridoma cell lines DSM ACC2842 or DSM ACC2879 one can compare its activity in blocking assays or competition assays.

It is to be understood that the affinity of an antibody to an antigen depends on the structure of the antibody and of the antigen, and on the actual assay conditions. The affinity can be for example determined under conditions favoring monovalent interactions between the antibody and the antigen. Kd can be determined by methods known in the art. Kd of a given combination of antibody and antigen is preferably determined by ELISA, wherein a constant amount of immobilized antigen is contacted with a serial dilution of a known concentration of a purified antibody, preferably a monovalent antibody, for example scFv or Fab fragment. Kd is then determined as the concentration of the antibody where half-maximal binding is observed. Alternatively, Kd of a monovalent interaction of an antibody and an antigen is determined by Biacore analysis as the ratio of on rate (kon) and off rate (koff.).

Lower values of Kd indicate a stronger binding of the antibody to the antigen than higher values of Kd. Thus, in the context of the application, an antibody is considered to be "specifically binding an antigen (of interest), when the dissociation constant (Kd), preferably determined as described above, and further preferably determined in a monovalent interaction, is at most 1×10E-7M, preferably approx. 1×10E-8M, preferably 1×10E-9M to 1×10E-12M.

Specifically, the antibody according to the invention which has the same specificity to an epitope of the MERV envelope glycoprotein as an antibody produced by the hybridoma cell line DSM ACC2842 has a Kd of approx. 1×10E-7M, preferably approx. 6.7×10E-8M, preferably 1×10E-9M, preferably 1×10E-10M, preferably 1×10E-11M, preferably 1×10E-12M as determined by biacore against the G1 peptide.

As an alternative, the antibody according to the invention which has the same specificity to an epitope of the MERV envelope glycoprotein as an antibody produced by the hybridoma cell line DSM ACC2879 has a Kd of approx. 1×10E-7M, preferably approx. 1×10E-8M, preferably 1×10E-9M, preferably 1.10E-10M, preferably 1×10E-11M, preferably 1×10E-12M as determined by biacore against the transmembrane protein of MERV.

According to a specific embodiment, the antibody can compete with or reduces the binding of an antibody described herein for binding to the same antigen as an antibody produced by hybridoma cell lines DSM ACC2842 or DSM ACC2879. In particular, the present invention encompasses antibodies that compete with antibodies produced by hybridoma cell lines DSM ACC2842 or DSM ACC2879 or an antigen-binding fragment thereof for binding to MERV. In a specific embodiment, the invention encompasses an antibody that reduces the binding of the antibodies produced by hybridoma cell lines DSM ACC2842 or DSM ACC2879 to by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more relative to a control such as PBS in an competition assay known in the art, for example in an ELISA competition assay.

The invention covers also the hybridoma cell lines which produce the inventive antibodies. Specifically a hybridoma cell line deposited as DSM ACC2842 at the DSMZ on May 10, 2007 and a hybridoma cell line deposited as DSM ACC2879 at the DSMZ on Jan. 16, 2008 are covered.

The invention also provides a method for isolating and/or identifying regions of an endogenous retrovirus in vitro using an antibody which specifically binds to and/or competes for binding to the same or a similar antigen with an antibody produced by the hybridoma cell lines DSM ACC2842 or DSM ACC2879.

The antibodies of the invention can be used for isolating and/or identifying melanoma cells in vitro.

Further, the antibodies can be used for the preparation of a pharmaceutical composition for the treatment or diagnosis of cancer disease, preferably of melanoma disease in an animal, preferably in a human.

In addition to the one or more antibodies, such a pharmaceutical composition can comprise additional suitable substances such as diluents, solvents, stabilizers, etc. These include, for example, physiological sodium chloride solutions, water, alcohols and other suitable substances which can be found, for example, in A. Kibble, "Handbook of Pharmaceutical Excipients", 3rd ed., 2000, American Pharmaceutical Association and Pharmaceutical Press.

Diagnosis of cancer, especially of melanoma remains a difficult challenge in surgical pathology, partly because of its high histological variability, cytomorphology, architecture and stromal components. Presently available biomarkers aimed at supporting diagnosis lack of sensitivity and specificity.

According to the present invention a diagnostic kit for the detection of cancer cells is also covered, preferably for the detection of melanoma cells, said kit comprising at least one container containing at least one antibody according to the invention.

A method for melanoma diagnosis using an antibody according to the invention comprising the steps of a. contacting a sample of possible cancer, preferably of melanoma origin with said antibody, which leads to an antibody-antigen reaction between the sample and said antibody, and
b. detecting and optionally quantifying said antibody-antigen reaction, wherein an antigen-antibody binding indicates the presence of cancer cells is also covered.

Further, a method of determining the concentration or presence of cancer cells in vitro using an antibody of the invention or a mixture of inventive antibodies is covered characterized in that the antibodies are associated with a label, the method comprising exposing cells in a test sample to the antibodies and determining the extent of binding by detecting the label.

Other advantages ensue from the attached figures and the description.

The foregoing description will be more fully understood with reference to the following examples. Such examples are, however, merely representative of methods of practicing one or more embodiments of the present invention and should not be read as limiting the scope of invention.

EXAMPLES

Example 1

Material and Methods

Antibodies

A monoclonal antibody recognizing an immunodominant sequence stretch of the MERV envelope protein (YQRSLK-FRPKGKPCPKE, SEQ ID NO: 1, National Center for Biotechnology Information accession number AX743231, amino acid sequence area envelope 214-230) was generated by immunizing female Balb/c mice with the peptide corresponding to the immunodominant envelope region coupled to KLH (PiCHEM, Graz, Austria). The hybridomas were selected on the basis of the supernatant's reactivity against the peptide in ELISA. The most reactive hybridoma, 1A1-5B10-B3, deposited at the DSMZ on May 10, 2007, was used to produce monoclonal antibody 5B10 (Genovac GmbH, Freiburg, Germany). Isotyping was performed using Isostrip kit (Roche, Basel, Switzerland) according to the manufacturer's instructions. The isotype of mAb 5B10 was IgG1.sub.k and the final concentration was 1 mg/ml in PBS. A purified mouse IgG1.sub.k (Becton Dickinson, San Jose, Calif.) was used as isotype control.

Cell Lines

Melanoma cell lines 518A2 (courtesy of Peter Schrier, University of Leiden, the Netherlands), A375 and SKMel28 (American Type Culture Collection, ATCC, Manassas, Va.), MelJuso (German Collection of Microorganisms and Cell Culture, DSMZ, Braunschweig, Germany), 6F (primary melanoma cells, Department of Dermatology, Medical University of Vienna, Austria) were maintained in DMEM (Invitrogen, Carlsbad, Calif.) containing 10% heat-inactivated fetal bovine serum and 1% antibiotic-antimycotic mix (both Gibco, Paisley, UK).

NHEM-Neo (Normal Human Epidermal Melanocyte-Neonatal, ATCC) were cultivated in melanocyte basal medium containing 1% antibiotics and 10% epidermal melanocyte growth supplement (Cell Systems Biotechnologies, St. Katharinen, Germany). All cells were grown at 37° C. in a 5% $CO_2$ air-humidified atmosphere.

Vero cells (African Green Monkey Kidney, ECACC WHO seed 0693) were maintained in DMEM (Invitrogen, Carlsbad, Calif.) containing 10% heat-inactivated fetal bovine serum and 1% antibiotic-antimycotic mix (both Gibco, Paisley, UK).

MERV-Env Transfection of Vero Cells

Transient transfection of Vero cells with MERV env-plasmid was performed using VeroFect (OZ Biosciences, Marseille, France). $2 \times 10^4$ cells were seeded in one well of a 6-well-plate and incubated over night. For transfection, 2 solutions were prepared, one containing 4 µg plasmid DNA in 100 µl of DMEM (Gibco, Paisley, UK) without FCS and antibiotics, and the other containing 8 µl of VeroFect in 100 µl of DMEM without FCS and antibiotics. These two solutions were combined and incubated at room temperature for 20 min to form DNA-VeroFect-complexes. Cells were supplemented with 2 ml of fresh DMEM with FCS, and antibiotics and DNA-VeroFect-complexes were added. Cells were incubated at 37° C. for 24 hours before staining. Cells incubated with transfection mix without plasmid DNA were used as negative control.

Immunocytochemistry—Immunohistochemistry

For immunocytochemistry studies, cells were grown on 8-well chamber slides for 48 hours (LabTec, Nalge Nunc Int., Rochester, N.Y.) and fixed in 4% cold paraformaldehyde for 15 minutes. Immunohistochemistry studies were performed on conventional formalin-fixed paraffin tissue sections mostly prepared as tissue arrays after pre-treatment in antigen retrieval solution (DAKO, Glostrup, Denmark) at 80° C. o/n.

Staining was performed by incubation in a humified box with primary antibody mAb 5B10 at a final concentration of 50 µg/ml and 3 h incubation at 37° C. Detection was performed using goat-anti-mouse HRP-conjugated secondary antibody (Santa Cruz Biotechnology, Heidelberg, Germany) diluted 1:25 for 30 minutes at room temperature. AEC Chromogen (DAKO, Glostrup, Denmark) was used as substrate for 5-10 minutes and counterstaining was performed with Mayer's hematoxylin for 20 seconds, followed by washing with tap water for 2-5 minutes. Slides were mounted using Aquatex (Merck, Darmstadt, Germany). For negative control, the primary antibody was replaced with mouse isotype IgG at a concentration equal to that of the primary antibody. MERV-negative cell lines as well as tissue sections containing normal adjacent tissue were simultaneously tested as second negative control.

ELISA Screening

The MERV-derived peptide used for ELISA sera screening (accession number AX743231, envelope amino acid stretch 214-230, subsequently called G1) as well as a reference peptide (GGTGMTKTTNTDSGHSG, SEQ ID NO: 4) were synthesized at >90% purity (PiCHEM, Graz, Austria). The purity of these peptides was assessed by HPLC and MS. Peptides were diluted with dimethylsulfoxide to a final concentration of 3 mg/ml.

Antibodies reactive with MERV envelope epitopes were detected by indirect ELISA as described previously[9]. 96-well microtiter plates (Nunc, Rochester, N.Y.) were coated with 0.25 µg/well of 17mer-peptides (G1, reference peptide) over night and blocked with 2% bovine serum albumin in 0.1% v/v Tween 20 containing PBS. The plates were then washed and incubated with hybridoma samples (diluted 1:100) or human melanoma serum samples (diluted 1:200). For murine hybridomas, antibody binding was detected with the help of alkaline-phosphatase conjugated goat anti-mouse IgG antibody (Tropix, Bedford, Mass.), and for human sera with alkaline-phosphatase conjugated goat-anti-human IgG antibody (Bethyl Inc., Bethesda, Md.). After one hour, the plates were washed and p-nitrophenylphosphate (Sigma Aldrich) was added. Absorbance was measured at 405 nm (BDL Immunoskan Plus).

Each sample was measured in triplicate for each peptide (G1, reference peptide). The mean values of the triplicates were calculated and a final ELISA signal for each sample was determined as the difference between mean values of MERV candidate epitope and reference peptide.

Sera and Tissue Collection

Sera and tissue samples from melanoma patients (diagnosis was established by routine histopathology at the Department of Dermatology, Petzelbauer P.) were collected at the Department of Dermatology, Medical University of Vienna, Austria. Staging of patients and classification of sera followed the 2001 American Joint Committee on Cancer guidelines (Balch, C. M. et al. *CA Cancer J. Clin.* 54, 131-49; (2004). Usage of patient sera and clinical data was approved by the ethical committee of the Medical University of Vienna. Confidentiality of the study subjects was guaranteed by sample coding. S-100-positive melanoma tissue arrays were obtained from US Biomax, Rockville, Md. (array ME801) as additional sample source.

Results:

Using an immunodominant peptide of MERV's envelope protein (G1 peptide) as antigen, we generated monoclonal antibody (mAb) 5B10. Specificity of mAb 5B10 staining towards MERV env was proved by two independent methods. Pre-incubating mAb 5B10 with a 100 molar excess of its target peptide G1 abolished reactivity against the peptide in ELISA and reactivity in immunohistochemistry staining. To correlate G1 specificity with MERV env reactivity, MERV-negative Vero cells were transiently transfected with MERV-env coding pIRES-EGFP-env plasmid, resulting in strong MERV-env expression as demonstrated in immunocytochemistry staining with mAb 5B10 (figure not shown).

Using mAb 5B10 immunocytochemistry staining of melanoma cell lines and human melanocytes was performed. Antibody 5B10 reacted with all melanoma cell lines examined (SKMel28, 518A2, MelJuso, A375 and 6F). The antibody gave no significant signal with cultured melanocytes (NHEM) and Vero cells, which served as negative control. The isotype control antibody neither stained the melanoma cell lines nor the melanocytes (results not shown).

We next tested whether mAb 5B10 could be used in paraffin immunohistochemistry to differentiate malignant from benign melanocytic lesions. A total of 186 melanocytic lesions were analyzed for reactivity to mAb 5B10. 58 dermal nevi, 81 primary melanomas and 47 melanoma metastases were screened. Immunohistochemistry with mAb 5B10 was exclusively performed on S100-positive tissue sections to ensure melanosomal origin. The intensity of the 5B10 cytoplasmatic staining pattern was classified as negative, moderate or strong. For each tissue section, hematoxylin-eosin (HE), 5B10, isotype control (ISO) as well as S-100 staining were performed. The results of 5B10 immunohistochemistry are summarized in Table 1. Staining for MERV envelope protein was positive in 75 (93%) of 81 cases of primary melanoma, and in 43 (91%) of 47 melanoma metastases when considering both, moderate and strong staining. 2 out of 58 (3%) cases of dermal nevi were moderately reactive.

TABLE 1

Summary of immunohistochemistry on melanocytic lesions using mAb 5B10

| Sample type | No. of patients | Negative | Moderately positive | Strongly positive |
|---|---|---|---|---|
| Dermal nevi | 58 | 56 (97%) | 2 (3%) | 0 |
| Primary melanomas | 81 | 6 (7%) | 19 (23%) | 56 (70%) |
| Melanoma metastases | 47 | 4 (9%) | 15 (32%) | 28 (59%) |

This antibody can be used for immunohistochemistry on conventional formalin-fixed paraffin sections. With the help of this antibody we found a strikingly high prevalence for malignancy, which indicates that mAb 5B10 can be used to discriminate between benign and malign melanocytic lesions.

We analyzed whether reactivity of tissue determined with mAb 5B10 correlates with a humoral immune response. Using melanoma tissue sections and sera samples, both taken at the same time point, we performed immunohistochemistry with mAb 5B10 and serum-ELISA assay, using G1 versus reference peptide as antigen. For the 16 screened patients, strongly positive immunohistochemistry (n=8) correlated with higher values in sera-ELISA (mean value of optical density 0.321), while patients with negative tissue staining (n=3) had low sera reactivity (mean value of optical density 0.080).

Example 2

Evaluation of the Inhibitory Effect of a Monoclonal Antibody 5B10 on Melanoma Tumor Development in Nude Mice The goal of this mouse study was to evaluate the monoclonal antibody (5B10) for its inhibitory effect on melanoma tumor development upon intravenous application. Nu/nu mice are a standard animal model for the induction of human tumor cells and multiple in vivo treatment strategies in oncological research. Based upon their innate NK-cell activity nu/nu mice allow us to study antibody dependent cellular cytotoxicity induced by mAb-treatment in vivo.

Inoculation of tumors was performed using 7×10E6 cells/mouse of melanoma cell line 518A2 s.c. in the right scapular area. There were two groups of mice of 8 mice/group treated three times per week intravenously with mAb 5B10 versus PBS immediately after tumor cell inoculation (from day 0) in volume of 100 µl. Tumor growth started between day 6 and 17 after tumor cell inoculation. Comparing group 1 (mAb 5B10 treated) versus PBS control group 2, tumors were hold at steady-state during mAb-5B10 treatment whereas tumors in the control group were expanding indicating a therapeutic effect of mAb 5B10 treatment.

Example 3

Expression and Purification of Recombinant MERV Transmembrane Domain (TM)

The ectodomain of the MERV transmembrane domain (amino acids 488-586) was amplified as described previously (Buscher et al, Melanoma Res 16:223-34. 2006). The amplified DNA revealed 100% sequence similarity with published MERV sequence (NCBI Accession number DQ058016). The amplicon was cloned into the pMal Vector (New England Biolabs) and transformed into E. coli. The expressed transmembrane protein fused N-terminally to a 42 kDa maltose-binding protein (MBP2) was purified using an amylase chromatography column. The expressed recombinant protein comprises about 55 kDa (MBP-protein: 42 KDa, TM-protein: 13 kDa). Buffer: 20 mM Tris/HCl, 200 mM NaCl, 1 mM EDTA, 10 mM Maltose.

Antibodies

A monoclonal antibody recognizing the MERV transmembrane domain was generated by immunizing female Balb/c mice with the ectodomain of the MERV transmembrane protein (BioGenes GmbH, Berlin, Germany). Hybridomas were selected on the basis of reactivity of the corresponding hybridoma supernatants against the immunization protein in ELISA and immunfluorescence experiments using melanoma cell lines. The most reactive and specific hybridoma anti-MBP-TM clone 33-8-7. This hybridoma was deposited at the DSMZ (DSMZ-Deutsche Sammlung von Mikroorganismen and Zellkulturen GmbH, Mascheroder Weg 1b, D-38124, Braunschweig, Germany) on Jan. 16, 2008, deposit number DSM ACC2879 and was used to produce the monoclonal antibody TM 33-8-7 (BioGenes GmbH, Berlin, Germany). Isotyping was performed using "Mouse Monoclonal Antibody Isotyping kit" (Roche, Basel, Switzerland) according to the manufacturer's instructions. The isotype of mAb TM 33-8-7 was IgG2a.sub.k. A purified mouse IgG2a.sub.k (BD Pharmingen, San Diego, Calif.) was used as isotype control.

Malignant Melanoma Tissue Array

Immunohistochemical paraffin studies were performed on conventional formalin-fixed paraffin sections (Malignant melanoma tissue array # ME801, US Biomax, USA) containing 80 different melanoma tissue sections per slide (tissue specificity was confirmed with anti-S100 antibody by standard IHC) and on tissue samples collected at the Department of Dermatology, Medical University Vienna. In total, tissue array staining was done on 160 primary melanoma tissues, 76 melanoma metastases and 192 dermal naevi.

After deparaffinization in xylene and following hydration in graded alcohols, epitope retrieval was performed by over night treatment in antigen retrieval solution (DAKO, Heidelberg, Germany) at 80° C. Endogenous peroxidase was suppressed by incubation with 3% $H_2O_2$. Slides were incubated with primary antibodies for 3 h at 37° C. Detection was performed using goat anti mouse HRP-conjugated secondary antibody (Santa Cruz Biotechnology, USA) diluted 1:25 for 30 minutes at room temperature. As substrate AEC chromogen (DAKO, Germany) was used for 5-10 minutes and counterstaining was performed by use of Mayer's hematoxylin for 20 seconds followed by washing with tap water for 2-5 minutes. Finally slides were mounted using Aquatex (Merck). For negative controls, the primary antibody was replaced with mouse isotype at a concentration equal to the primary antibody used. As second negative control, tissue sections containing normal adjacent tissue were simultaneously included on tissue arrays.

Tissue Array of Other Carcinomas

Immunohistochemical paraffin studies were done as described above. Following commercial tissue arrays were used:
CO1002: Colon and rectum carcinoma and normal tissue array
LC1004: Lung carcinoma tissue array
CR803: Multiple (uterine cervix) cervical squamous cancer tissue array
TH208: Thyroid cancer tissue microarray Epitope Mapping MERV-TM-derived peptides for epitope mapping were synthesized by Iris Biotech GmbH, Germany. The purity of these peptides was assessed by HPLC and MS. Peptides were diluted with dimethylsulfoxide to a final concentration of 3 mg/ml. 96-well microtiter plates (Nunc, Rochester, N.Y.) were coated with 0.25 µg/well of each peptide over night and blocked with 2% bovine serum albumin in PBS containing 0.1% v/v Tween 20. The plates were then washed and incubated with antibody. Antibody binding was detected with alkaline-phosphatase conjugated goat anti-mouse IgG antibody (Tropix, Bedford, Mass.). After one hour, plates were washed and p-nitrophenylphosphate substrate (Sigma Aldrich) was added. Absorbance was measured at 405 nm. Each sample was measured in triplicate for each peptide. The mean values of the triplicates were calculated and a final ELISA signal for each sample was determined.

In Vivo Antitumor Activity

Pathogen-free male and female nu/nu mice were obtained from Charles River Laboratories, Sulzfeld, Germany and randomly assigned to two groups of six mice (treatment starts immediately after tumor cell inoculation) and two groups of ten mice (treatment starts at tumor size of 40 $mm^3$). The mice were injected subcutaneously into the left shoulder with 7×10^6 human melanoma cells (518 A2) suspended in Matrigel (BD Biosciences, San Jose, Calif.) and PBS. Mice were treated 3 times per week with monoclonal antibody TM 33-8-7 immediately after tumor cell inoculation or when tumors reached a volume of 40 $mm^3$. Control group received Ringer solution only. Once tumors became evident, the tumor size was measured every two to three days using a caliper [volume=(width$^2$× length)×0.52].

Results:

Malignant Melanoma Tissue Array

Monoclonal antibody TM 33-8-7 turned out to be most sensitive and specific among all screened anti-TM monoclonal antibodies. Tissue array staining was done on 160 primary melanoma tissues, 76 melanoma metastases and 192 dermal naevi. Results on nevi, primary tumor tissues and metastases tissues are presented in table 1.

TABLE 1

Summary of immunohistochemistry on melanocytic lesions using mAb TM 33-8-7.

| Sample type | No. of samples | Negative | Positive |
|---|---|---|---|
| Primary melanoma | 160 | 31 (19%) | 129 (81%) |
| Melanoma metastases | 76 | 12 (16%) | 64 (84%) |
| Dermal nevi | 192 | 185 (96%) | 7 (4%) |

Table 1 shows the three different sample types and the corresponding number of analyzed samples as well as staining results: 'negative' stands for no detectable staining and 'positive' indicate staining.

Staining of the MERV transmembrane domain appears as red-brown cytoplasmatic staining pattern. Staining for MERV transmembrane domain was positive in 129 (81%) out of 160 cases of primary melanoma, and in 64 (84%) out of 76 melanoma metastases. Only 7/192 (4%) cases of dermal nevi were reactive.

For assuring specificity of staining we established a competition assay by pre-absorbing anti-TM antibody 33-8-7 with an approximately 10 molar excess of its target protein. After preincubation over night at 4° C. the antibodies showed no reactivity against the target in ELISA. Incubation of anti-TM antibody 33-8-7 with recombinant TM protein resulted in highly reduced staining pattern. These data clearly indicate the specific reactivity of monoclonal antibody with the MERV envelope fragment on melanoma cells.

Tissue Arrays of Other Tumors

Monoclonal antibody TM 33-8-7 also detected other tumors like colon carcinoma & colorectum carcinoma, lung carcinoma, cervical carcinoma as well as thyroid carcinoma (table 2).

TABLE 2

Summary of immunohistochemistry on different tumors using mAb TM 33-8-7

| | positive tested malignant tissues/total amount of malignant tissues | positive tested benign tissues/total amount of benign tissues |
|---|---|---|
| colon carcinoma & colorectum carcinoma | 9/36 | 0/19 |
| lung carcinoma | 25/90 | 1/8 |
| cervical carcinoma | 20/70 | 0/5 |
| thyroid carcinoma | 66/180 | 0/27 |

The result indicates that mAb TM 33-8-7 is also reactive with carcinomas other than melanoma.

Epitope Mapping

To determine whether monoclonal antibody TM 33-8-7 recognizes any immunodominant regions, peptides along the MERV transmembrane domain were synthesized and tested via ELISA screening. In a first screening round, 8 peptides within the transmembrane region were synthesized based on bioinformatic calculation. Only one peptide which is located within the immunosuppressive domain appeared positive. Based on that, 26 overlapping peptides covering the whole immunosuppressive domain were synthesized and tested for their reactivity with mAb TM 33-8-7.

Figure 1:
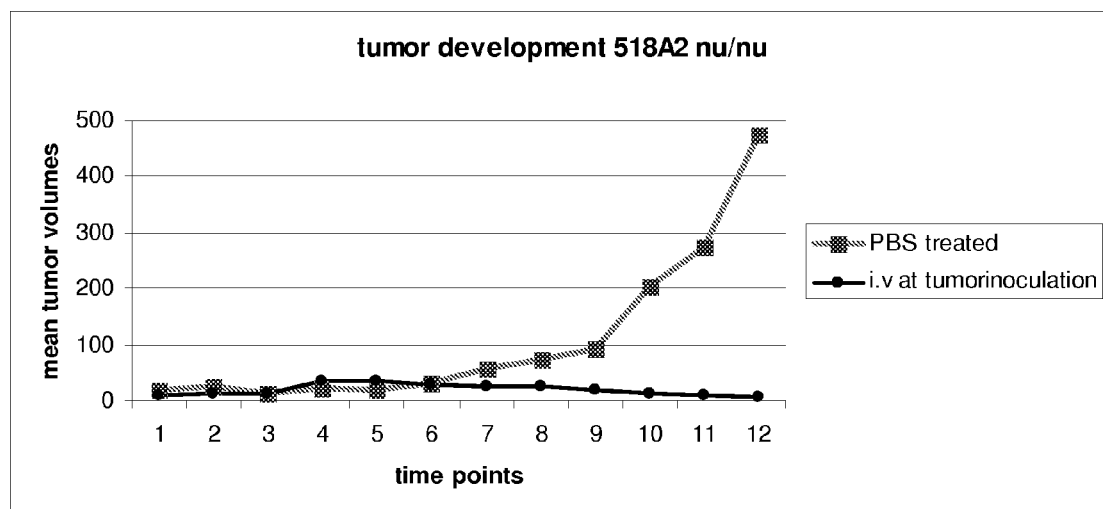
FIG. 1 shows the in vivo effect of treatment with 5B10 antibody on melanoma tumor development when started immediately after tumor cell injection. Tumors were hold at steady-state during mAb-5B10 treatment whereas tumors in the control group were expanding.
Figure 2:
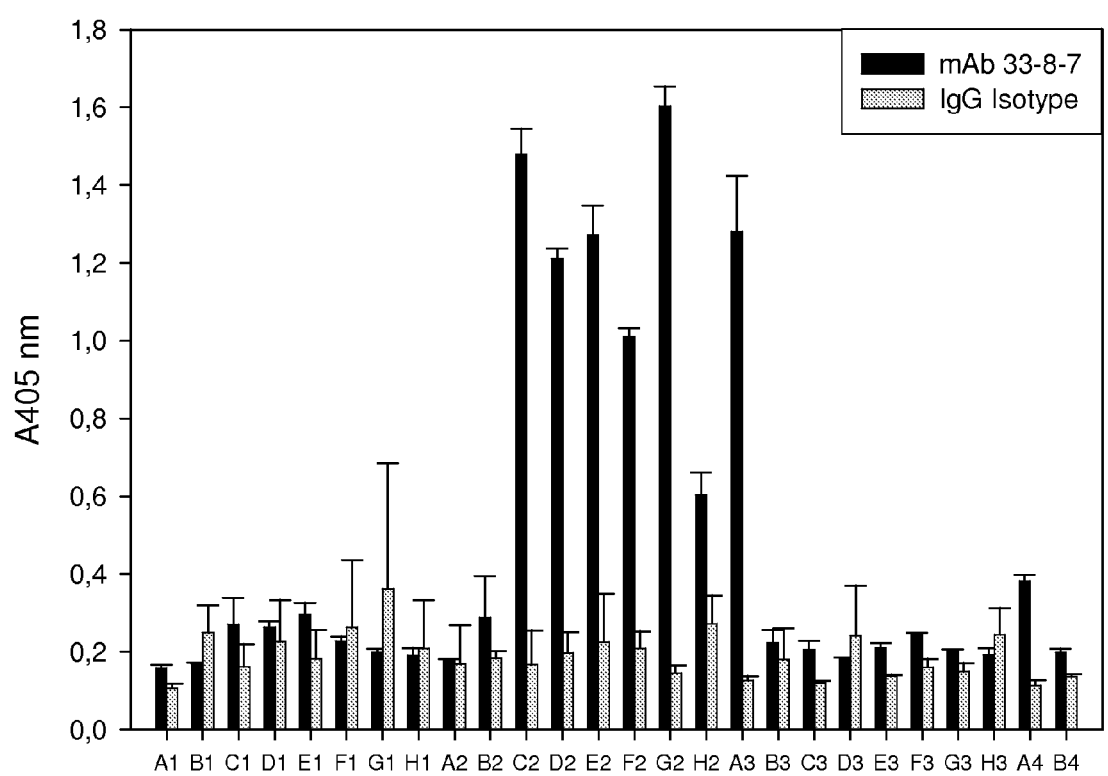
FIG. 2 shows the reactivity of mAb TM 33-8-7 with synthetic peptides measured by ELISA. Black bars: mAb 33-8-7; grey bars: mouse IgG isotype control.

FIG. 2 shows the reactivity of mAb TM 33-8-7 with synthetic peptides measured by ELISA. Black bars: mAb TM 33-8-7; grey bars: IgG isotype control group. 7 consecutive overlapping peptides [C2: HRFQLQCDWNTSDFC (SEQ ID NO: 5), D2: RFQLQCDWNTSDFCI (SEQ ID NO:6), E2: FQLQCDWNTSDFCIT (SEQ ID NO: 7), F2: QLQCDWNTSDFCITP (SEQ ID NO: 8), G2: LQCDWNTSDFCITPQ (SEQ ID NO: 9), H2: QCDWNTSDFCITPQI (SEQ ID NO: 10), A3: CDWNTSDFCITPQIY (SEQ ID NO: 11)] showed strong reactivity with mAb TM 33-8-7, revealing that the core sequence of the epitope corresponds to the amino acid sequence HRFQLQCDWNTSDFCITPQIY (SEQ ID NO: 2). Applying a Students t-test for comparing the distribution of background and signal values reaches a level of significance of $p<0.000001$.

Based on the given experimental data the core epitope for the given antibody is covered by the overlapping peptides C2, D2, E2, F2, G2, H2, A3.

Example 4

Evaluation of the Inhibitory Effect of a mAb TM 33-8-7 on Melanoma Tumor Development in Nude Mice The goal of the mouse study was to evaluate monoclonal antibody TM 33-8-7 for its inhibitory effect on melanoma tumor development upon i.t. injection. Nu/nu mice are a standard animal model for the induction of human tumor cells and multiple in vivo treatment strategies in oncological research. Based upon their innate NK-cell activity nu/nu mice allowed us to study antibody dependent cellular cytotoxicity induced by mAb-treatment in vivo.

Inoculation of tumors was performed using $7\times10^6$ cells/mouse of melanoma cell line 518A2 s.c. in the right scapular area.

2 groups of 6 mice per group were treated 3 times per week (4 weeks in total) immediately after tumor cell injection. Treatment was done i.v. with 15 mg/kg body weight mAb TM 33-8-7 versus PBS. Tumors were hold at a steady-state level during mAb TM 33-8-7 treatment (340 mm$^3$ after final treatment), whereas tumors in the control group expanded up to 1207 mm$^3$, indicating a therapeutic effect of mAb TM 33-8-7 treatment (FIG. 3).

FIG. 3 shows the anti-tumor activity of mAb TM 33-8-7 against melanoma xenografts in vivo. Treatment starts (day 1) immediately after tumor cell injection (day 0). White bars: PBS control group; shaded bars: mAb TM 33-8-7 group.

2 groups of mice of 10 mice per group were treated 3 times per week (4 weeks in total) at a tumor size of 40 mm$^3$. Treatment was done i.v. with 10 mg/kg body weight mAb TM 33-8-7 versus PBS. Tumor size reached approximately 40 mm$^3$ 4 weeks after tumor cell inoculation. In the control group, tumors reached an average size of 4943 mm$^3$ after the treatment period. In the treatment group, tumor growth was reduced to an average size of 1858 mm$^3$ (FIG. 3).

FIG. 4 shows the anti-tumor activity of mAb TM 33-8-7 against MERV transmembrane domain xenografts in vivo. Treatment started at a tumor volume of 40 mm$^3$. White bars: PBS control group; shaded bars: mAb TM 33-8-7 group.

Example 5

Treatment of Manifest Tumors Using 5B10 Antibody

For testing the effect of GHB-5B10 on manifest tumors the following setting was chosen:

PBS control group: 10 animals
GHB-5B10 group: 10 animals
Melanoma cell line 518A2
Mean treatment interval: 3 days
Total number of intervals: 14
Treatment start at tumor volume >=40 $mm^3$
Treatment stop at tumor volume >=4000 $mm^3$ Animals were inoculated with the melanoma cell line, and after a tumor volume of >40 mm3 was identified the animals were randomized for the PBS control group and the GHB-5B10 treatment group.

FIG. 5: For analysis tumor volumes >=4000 $mm^3$ were forwarded with this volume also for the subsequent treatment days. In the PBS group a massive expansion of tumor mass is found between day 15 and day 21, whereas in the GHB-5B10 group increase in tumor mass is delayed.

PBS group: mean, error of mean and standard deviation of tumor volume ($mm^3$) plotted versus treatment interval.

GHB-5B10 group: mean, error of mean and standard deviation of tumor volume ($mm^3$) plotted versus treatment interval.

In the PBS group 9 out of 10 animals develop a tumor > 4000 $mm^3$ at day 42.

In the GHB-5B10 group increase in tumor mass is delayed, 5 out of 10 animals develop a tumor >4000 $mm^3$ at day 42.

FIG. 6: Number of animals with tumor mass below 4000 $mm^3$ as monitored at each treatment interval. In the PBS group 9 out of 10 animals develop a tumor >4000 $mm^3$, whereas only 5 out of 10 animals develop a tumor >4000 $mm^3$ in the GHB-5B10 group.

Example 6

Measurement of In Vitro ADCC Activity

One of the most important mechanisms of action of therapeutic mAb is Antibody-dependent cellular cytotoxicity (ADCC). Nude mice, although lacking in functional T-cell-mediated immunity, retain the ability to mount $F_c$-dependent immune responses mediated by effector cells (ADCC).

The ability of MERV-specific mAb 5B10 and TM-33 to mediate ADCC was assessed by using spleen cells of a nude mouse as effector cells for the study of antibody-dependent cellular cytotoxicity (ADCC) assay in vitro.

Single-cell suspensions of the spleen were prepared by gently teasing the tissue through a nylon-mesh strainer (70-μm Cell Strainer; Falcon, Becton Dickinson, Franklin Lakes, N.J.). The cell suspensions were washed twice and resuspended in culture medium (RPMI 1640 containing 2.0 mM L-glutamine, 100 IU/ml penicillin, 100 μg/ml streptomycin and 10% heat-inactivated fetal calf serum.

10.000 melanoma target cells were preincubated with 20 g of antibody (mAb 5B10, mAb TM-33 versus an irrelevant non-binding antibody called MAK) in round-bottom 96-well plates for 2 hours at 37° C. Then the effector cells were dispensed into the wells at a ratio of 100:1. After incubation for 4 h at 37° C. the plates were centrifuged and the supernatants were harvested.

The cytotoxicity induced was determined by the lactate dehydrogenase activity in the supernatants using a nonradioactive cytotoxicity assay kit (Promega, Madison, Wis.). The percentage of specific cytolysis was calculated from the activities of samples according to the formula, % specific lysis($ADCC$)=100×($E-S_E-S_T$)/($M-S_T$)

where E represents the experimental release (activity in the supernatant from target cells incubated with antibody and effector cells), $S_E$ is the spontaneous release in the presence of effector cells, $S_T$ is the spontaneous release of target cells, and M is the maximum release of target cells released from target cells lysed with 9% Triton X-100).

The average absorbance of triplicate determinations was used to calculate the percentage of ADCC-mediated cytotoxicity (Table 3).

|  | experimental | target spont. | effector spont. | max. release | ADCC |
| --- | --- | --- | --- | --- | --- |
| 5B10 | 2.41 | 0.835 | 1.135 | 2.901 | 21.30% |
| TM-33 | 2.501 | 0.636 | 1.113 | 2.901 | 33.20% |
| MAK | 1.567 | 0.652 | 1.217 | 2.901 | 0.00% |

The invention claimed is:

1. An antibody characterized in that it is produced by the hybridoma cell line having DSMZ accession number DSM ACC2879.

2. A hybridoma cell line having DSMZ accession number DSM ACC2879.

* * * * *

SEQUENCE LISTING

<160> NUMBER OF SEQ ID NOS: 11

<210> SEQ ID NO 1
<211> LENGTH: 17
<212> TYPE: PRT
<213> ORGANISM: Human endogenous retrovirus

<400> SEQUENCE: 1

Tyr Gln Arg Ser Leu Lys Phe Arg Pro Lys Gly Lys Pro Cys Pro Lys
1               5                   10                  15

Glu

<210> SEQ ID NO 2
<211> LENGTH: 21
<212> TYPE: PRT
<213> ORGANISM: Human endogenous retrovirus

<400> SEQUENCE: 2

His Arg Phe Gln Leu Gln Cys Asp Trp Asn Thr Ser Asp Phe Cys Ile
1               5                   10                  15

Thr Pro Gln Ile Tyr
            20

<210> SEQ ID NO 3
<211> LENGTH: 239
<212> TYPE: PRT
<213> ORGANISM: Human endogenous retrovirus

<400> SEQUENCE: 3

Asn Arg Ser Lys Arg Phe Ile Phe Thr Leu Ile Ala Val Ile Met Gly
1               5                   10                  15

Leu Ile Ala Val Thr Ala Thr Ala Ala Val Ala Gly Val Ala Leu His
            20                  25                  30

Ser Ser Val Gln Ser Val Asn Phe Val Asn Asp Trp Gln Lys Asn Ser
        35                  40                  45

Thr Arg Leu Trp Asn Ser Gln Ser Ser Ile Asp Gln Lys Leu Ala Asn
50                  55                  60

Gln Ile Asn Asp Leu Arg Gln Thr Val Ile Trp Met Gly Asp Arg Leu
65                  70                  75                  80

Met Ser Leu Glu His Arg Phe Gln Leu Gln Cys Asp Trp Asn Thr Ser
                85                  90                  95

Asp Phe Cys Ile Thr Pro Gln Ile Tyr Asn Glu Ser Glu His His Trp
            100                 105                 110

Asp Met Val Arg Arg His Leu Gln Gly Arg Glu Asp Asn Leu Thr Leu
        115                 120                 125

```
Asp Ile Ser Lys Leu Lys Glu Gln Ile Phe Glu Ala Ser Lys Ala His
    130                 135                 140

Leu Asn Leu Val Pro Gly Thr Glu Ala Ile Ala Gly Val Ala Asp Gly
145                 150                 155                 160

Leu Ala Asn Leu Asn Pro Val Thr Trp Val Lys Thr Ile Gly Ser Thr
                165                 170                 175

Thr Ile Ile Asn Leu Ile Leu Ile Leu Val Cys Leu Phe Cys Leu Leu
            180                 185                 190

Leu Val Cys Arg Cys Thr Gln Gln Leu Arg Arg Asp Ser Asp His Arg
        195                 200                 205

Glu Arg Ala Met Met Thr Met Ala Val Leu Ser Lys Arg Lys Gly Gly
    210                 215                 220

Asn Val Gly Lys Ser Lys Arg Asp Gln Ile Val Thr Val Ser Val
225                 230                 235
```

<210> SEQ ID NO 4
<211> LENGTH: 17
<212> TYPE: PRT
<213> ORGANISM: artificial
<220> FEATURE:
<223> OTHER INFORMATION: reference peptide for ELISA screening of MERV

<400> SEQUENCE: 4

```
Gly Gly Thr Gly Met Thr Lys Thr Thr Asn Thr Asp Ser Gly His Ser
1               5                   10                  15

Gly
```

<210> SEQ ID NO 5
<211> LENGTH: 15
<212> TYPE: PRT
<213> ORGANISM: Human endogenous retrovirus

<400> SEQUENCE: 5

```
His Arg Phe Gln Leu Gln Cys Asp Trp Asn Thr Ser Asp Phe Cys
1               5                   10                  15
```

<210> SEQ ID NO 6
<211> LENGTH: 15
<212> TYPE: PRT
<213> ORGANISM: Human endogenous retrovirus

<400> SEQUENCE: 6

```
Arg Phe Gln Leu Gln Cys Asp Trp Asn Thr Ser Asp Phe Cys Ile
1               5                   10                  15
```

<210> SEQ ID NO 7
<211> LENGTH: 15
<212> TYPE: PRT
<213> ORGANISM: Human endogenous retrovirus

<400> SEQUENCE: 7

```
Phe Gln Leu Gln Cys Asp Trp Asn Thr Ser Asp Phe Cys Ile Thr
1               5                   10                  15
```

<210> SEQ ID NO 8
<211> LENGTH: 15
<212> TYPE: PRT
<213> ORGANISM: Human endogenous retrovirus

<400> SEQUENCE: 8

```
Gln Leu Gln Cys Asp Trp Asn Thr Ser Asp Phe Cys Ile Thr Pro
1               5                   10                  15
```

```
<210> SEQ ID NO 9
<211> LENGTH: 15
<212> TYPE: PRT
<213> ORGANISM: Human endogenous retrovirus

<400> SEQUENCE: 9

Leu Gln Cys Asp Trp Asn Thr Ser Asp Phe Cys Ile Thr Pro Gln
1               5                   10                  15

<210> SEQ ID NO 10
<211> LENGTH: 15
<212> TYPE: PRT
<213> ORGANISM: Human endogenous retrovirus

<400> SEQUENCE: 10

Gln Cys Asp Trp Asn Thr Ser Asp Phe Cys Ile Thr Pro Gln Ile
1               5                   10                  15

<210> SEQ ID NO 11
<211> LENGTH: 15
<212> TYPE: PRT
<213> ORGANISM: Human endogenous retrovirus

<400> SEQUENCE: 11

Cys Asp Trp Asn Thr Ser Asp Phe Cys Ile Thr Pro Gln Ile Tyr
1               5                   10                  15
```